(12) United States Patent
Franjic

(10) Patent No.: US 11,583,182 B2
(45) Date of Patent: Feb. 21, 2023

(54) METHOD FOR MULTIMODAL TISSUE IMAGING BASED ON RESONANCE RAMAN EFFECT ON METAL BASED MRI CONTRAST AGENTS AND METHOD FOR IONIZING LASER PLUMES THROUGH ATMOSPHERIC PRESSURE CHEMICAL IONIZATION

(71) Applicant: SYNAPTIVE MEDICAL INC., Toronto (CA)

(72) Inventor: Kresmir Franjic, Toronto (CA)

(73) Assignee: Synaptive Medical Inc.

( * ) Notice: Subject to any disclaimer, the term of this patent is extended or adjusted under 35 U.S.C. 154(b) by 560 days.

(21) Appl. No.: 16/338,286

(22) PCT Filed: Jul. 24, 2017

(86) PCT No.: PCT/CA2017/050887
§ 371 (c)(1),
(2) Date: Mar. 29, 2019

(87) PCT Pub. No.: WO2018/014140
PCT Pub. Date: Jan. 25, 2018

(65) Prior Publication Data
US 2019/0269329 A1    Sep. 5, 2019

(30) Foreign Application Priority Data

Jul. 22, 2016  (CA) .................................. CA 2936994
Jul. 25, 2016  (CA) .................................. CA 2937047

(51) Int. Cl.
A61B 5/00     (2006.01)
A61B 5/055    (2006.01)
(Continued)

(52) U.S. Cl.
CPC .......... *A61B 5/0035* (2013.01); *A61B 5/0075* (2013.01); *A61B 5/055* (2013.01);
(Continued)

(58) Field of Classification Search
CPC ..... A61B 5/0035; A61B 5/0075; A61B 5/055; A61B 2090/397; A61B 2576/00;
(Continued)

(56) References Cited

U.S. PATENT DOCUMENTS

2015/0065858 A1* 3/2015 Chen .................. A61K 49/1833
                                                    600/431
2015/0252061 A1* 9/2015 Mazitschek ............... C07F 5/02
                                                    544/179
(Continued)

FOREIGN PATENT DOCUMENTS

WO    WO-2010111066 A2 *  9/2010  ......... A61K 41/0052

OTHER PUBLICATIONS

Anon, 2020. Metal to Ligand and Ligand to Metal Charge Transfer Bands. Available at: https://chem.libretexts.org/@go/page/1773 [Accessed Mar. 29, 2022]. (Year: 2020).*
(Continued)

*Primary Examiner* — Amanda Lauritzen Moher
*Assistant Examiner* — Delia M. Appiah Mensah

(57) ABSTRACT

Disclosed herein is a method for multimodal imaging during a medical procedure using magnetic resonance imaging (MRI) and Raman optical imaging which involves administering an MRI imaging contrast agent that a chemical structure having charge-transfer electronic transitions. The tissue is imaged using and MRI device and the tissue is illuminated with excitation light that has spectral components that are approximately tuned close to one of the charge-transfer electronic transitions thereby producing enhanced Raman optical signals which are analyzed to
(Continued)

produce Raman imaging data followed by registering the MRI and Raman imaging data. The present disclosure also provides a method for ionizing laser plumes through atmospheric pressure chemical ionization.

7 Claims, 8 Drawing Sheets

(51) Int. Cl.
G01R 33/48 (2006.01)
G01R 33/56 (2006.01)
A61B 90/00 (2016.01)
A61K 49/00 (2006.01)
A61K 49/10 (2006.01)
H01J 49/04 (2006.01)
H01J 49/16 (2006.01)
G01N 30/72 (2006.01)

(52) U.S. Cl.
CPC ........ *A61K 49/0002* (2013.01); *A61K 49/103* (2013.01); *A61K 49/106* (2013.01); *G01N 30/72* (2013.01); *G01R 33/4808* (2013.01); *G01R 33/5601* (2013.01); *H01J 49/0463* (2013.01); *H01J 49/168* (2013.01); *A61B 2090/397* (2016.02); *A61B 2576/00* (2013.01)

(58) Field of Classification Search
CPC .............. A61K 49/103; A61K 49/0002; A61K 49/106; G01R 33/4808; G01R 33/5601; H01J 49/0463; H01J 49/168
See application file for complete search history.

(56) References Cited

U.S. PATENT DOCUMENTS

2015/0351860 A1* 12/2015 Piron ................... A61B 5/055
600/417
2016/0000329 A1 1/2016 Kircher et al.

OTHER PUBLICATIONS

PCT ISR and Written Opinion from PCT/CA2017/050887 dated Nov. 16, 2017, 10 pgs.

Kircher et al., "A Brain Tumor Molecular Imaging Strategy Using a New Triple-Modality MRI-Photoacoustic-Raman-Nanoparticle", Nature Medicine, 2012:18(5):829-834. doi:10.1038/nm 2721.

Burke et al., "Investigation of $Gd_3N@C_{2n}(40<n<44)$ family by Raman and inelastic electron tunneling spectroscopy." Phys. Rev. B81, 115423—Published Mar. 15, 2010, dx.doi.org/10.1103/PhysRevB.81.115423.

* cited by examiner

METHOD FOR MULTIMODAL TISSUE IMAGING BASED ON RESONANCE RAMAN EFFECT ON METAL BASED MRI CONTRAST AGENTS AND METHOD FOR IONIZING LASER PLUMES THROUGH ATMOSPHERIC PRESSURE CHEMICAL IONIZATION

CROSS-REFERENCE TO RELATED APPLICATION(S)

This document is a national stage entry application claiming the benefit of, and priority to, International Application No. PCT/CA2017/050887, filed on Jul. 24, 2017, and entitled "METHOD FOR MULTIMODAL TISSUE IMAGING BASED ON RESONANCE RAMAN EFFECT ON METAL BASED MRI CONTRAST AGENTS AND METHOD FOR IONIZING LASER PLUMES THROUGH ATMOSPHERIC PRESSURE CHEMICAL IONIZATION;" Canadian Patent Application No. 2,936,994, filed on Jul. 22, 2016, and entitled "METHOD FOR MULTIMODAL TISSUE IMAGING BASED ON RESONANCE RAMAN EFFECT ON METAL BASED MRI CONTRAST AGENTS;" and Canadian Patent Application No. 2,937,047, filed on Jul. 22, 2016, and entitled "METHOD FOR IONIZING LASER PLUMES THROUGH ATMOSPHERIC PRESSURE CHEMICAL IONIZATION;" all of which are hereby incorporated by reference in their entirety.

FIELD

The present disclosure relates to use of a contrast imaging agent that can provide imaging contrast for both MRI and optical imaging. More particularly, the present disclosure relates to a method involving use of a contrast agent during acquisition of MRI and optical images of tissue whereby independently measuring the spatial distribution of the contrast agent within a tissue using MRI and optical images, spatial correlations between MRI and optical images can be established. The present disclosure also relates to a method for ionizing laser plumes using atmospheric pressure chemical ionization (APCI). More particularly, in the present method laser plumes are ionized by intercepting the plume with an ionized gas jet where the ionized jet contains dopant molecules that are previously ionized through an atmospheric pressure chemical ionization (APCI) process.

BACKGROUND

A) Method for Multimodal Tissue Imaging Based on Resonance Raman Effect on Metal Based MRI Contrast Agents Magnetic resonance imaging (MRI) is a widely used tissue imaging technique because it is non-invasive and it provides highly detailed 3D images. However, in cases like surgeries or research, there is often a challenge in spatially correlating optical images to MRI images of a tissue. The reason is that a tissue often moves uncontrollably or gets modified between MRI and optical imaging which causes loss of spatial correlations between the images. Frequent MRI scanning that would produce MRI images around the moment when optical images are acquired is impractical since MRI scans are long (typically between 15 and 90 min) and involve cumbersome instrumentation. An important example is a brain shift during neurosurgeries. Pre-op MRI scans are used for surgical navigation; however, during a craniotomy the brain often changes its position within the skull and/or can expand slightly through the hole in the skull which creates navigation errors and loss of correlation between pre-op MRI images and what a surgeon sees under an optical microscope.

For these reasons, it would be advantageous to have a contrast imaging agent that can provide imaging contrast for both MRI and optical imaging. In recent years, there have been efforts to develop multimodal imaging contrast agents. These multimodal contrast agents provide simultaneous contrast for different imaging modalities (MRI, ultrasound, Raman spectroscopy, etc.). This is advantageous since simultaneous contrast makes correlations between different imaging modalities possible thus increasing the overall informational content.

All multimodal contrast agents that combine MRI and optical modalities that have been disclosed so far are based on nanoparticles. While such approach shows great promise, this technology is still in the research phase and translation to clinical use can be long and uncertain. Thus developing a multimodal imaging method based on optical detection of existing chelated ion MRI contrast agents would be very advantageous.

B) Method for Ionizing Laser Plumes Through Atmospheric Pressure Chemical Ionization Mass spectrometry is one of the most important diagnostic techniques for determining molecular composition of a sample. In case of samples in condensed phase, several processing steps are required for mass spectrometry analysis: (a) desorption of sample molecules i.e. moving sample molecules from the condensed into the gas phase; (b) ionization of the desorbed molecules; and (c) coupling such ionized sample molecules into a mass spectrometer. In case of fragile molecules, such as a majority of biological molecules, the first two steps involving desorption and ionization are critical since desorption and ionization processes are generally energy intensive; so it is easy to put excess energy into the sample molecules which can cause their modification or break-up. Recent advances in laser ablation techniques, which desorb molecules though creation of laser ablation plumes, make possible desorption with imparting minimal excess energy into desorbed sample molecules; however, the most optimal ionization method of such desorbed molecules is still to be determined.

One of the standard methods for ionizing gas phase molecules is atmospheric pressure chemical ionization (APCI) which consists of putting a sharp metal object under high voltage in the vicinity of sample molecules which are desorbed in a gas atmosphere. Such a sharp metal object creates a corona discharge which generates charges that are transferred to the sample molecules either directly or indirectly through interactions with molecules in the gas atmosphere of liquid sample matrix molecules (e.g. water or alcohol) that are desorbed simultaneously with the sample molecules. APCI is a standard ionization technique and its general features are known to the person having ordinary skill in the art.

However, a standard APCI configuration is not an efficient method for ionizing laser plumes since laser plumes are highly localized in space and time while standard APCI corona discharges are not. For that reason, an APCI method that that delivers ions co-localized with gas phase sample molecules in time and space would be advantageous.

SUMMARY

The present disclosure provides a novel method for multimodal imaging based on simultaneous use of the same contrast agent for both MRI and optical imaging. The method involves application of a standard chelated ion (preferably $Gd^{3+}$) MRI contrast agent for enhancing the contrast of MRI images which are subsequently imaged during a surgery using resonance Raman spectroscopy.

The resonance Raman spectroscopy involves illuminating the tissue of interest with a monochromatic light whose wavelength is approximately tuned to charge-transfer electronic transitions of the contrast agent and analyzing the scattered light with a Raman detector. The Raman signals corresponding to molecular vibrational transitions coupled to the charge-transfer electronic transitions are greatly enhanced due to resonance effects making possible efficient optical imaging of the contrast agent. The acquired Raman optical image can be spatially registered to the corresponding MRI image by using registration fiduciary markers; anatomical landmarks; or 3D optical imaging. Another application of this method is guided tumor resection. Since such contrast agents tend to accumulate in tumor tissues, by optical imaging of such contrast agents it is possible to facilitate precise tumor resection.

In an embodiment the present disclosure provides a method for multimodal imaging during a medical procedure using magnetic resonance imaging (MRI) and Raman optical imaging, comprising:

a) administering, to a patient's tissue, a magnetic resonance imaging contrast agent that contains metal atoms, or metal ions, or metal complexes, said magnetic resonance imaging contrast agent having a chemical structure which includes charge-transfer electronic transitions;

b) imaging said tissue with a magnetic resonance imaging (MRI) device where said contrast agent provides imaging contrast enhancement and recording MRI imaging data;

c) illuminating said tissue with excitation light that has spectral components that are approximately tuned close to one of the charge-transfer electronic transitions of said contrast agent such that interaction of the excitation light with the charge-transfer electronic transitions produce Raman optical signals that are enhanced due to Raman resonance effects, and detecting and analyzing the optical Raman signals to produce Raman imaging data; and d) registering the MRI and Raman imaging data.

The present disclosure also provides a mass spectrometry system for analyzing molecular composition of a sample in a condensed phase, comprising:

a pulsed laser capable of ablating the surface of said sample atmospheric pressure thereby producing an ablation plume containing analyte molecules;

a gas delivery system for delivering a gas jet to the ablation plume, wherein said gas jet contains dopant molecules;

a metal object with a sharp tip placed in the vicinity of said gas jet;

a high voltage generator that is electrically connected to said metal object thereby creating a corona discharge at said sharp tip, wherein said corona discharge ionizes said dopant molecules in said gas jet;

and wherein said gas jet intercepts said laser ablation plume whereby at least one of subsequent direct or indirect collisions between said ionized dopant molecules and said analyte molecules results in ionization of several of said analyte molecules; and directing said ionized analyte molecules towards a mass spectrometer having an input positioned to intercept the ionized analyte molecules which are analyzed providing information about a molecular composition of said sample.

A further understanding of the functional and advantageous aspects of the present disclosure can be realized by reference to the following detailed description and drawings.

BRIEF DESCRIPTION OF THE DRAWINGS

Embodiments disclosed herein will be more fully understood from the following detailed description thereof taken in connection with the accompanying drawings, which form a part of this application, and in which.

DETAILED DESCRIPTION

Figure 1:
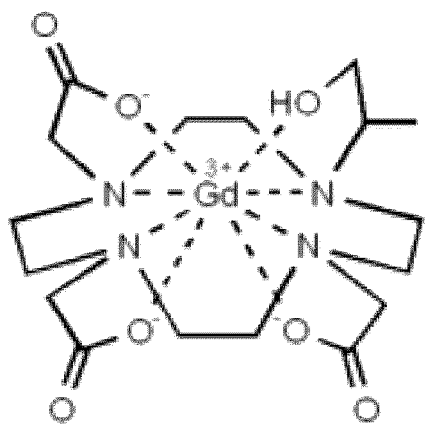
FIG. 1 shows the chemical structure of the gadolinium based contrast agent guadoteridol.

Various embodiments and aspects of the disclosure will be described with reference to details discussed below. The following description and drawings are illustrative of the disclosure and are not to be construed as limiting the disclosure. The drawings are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

While the teachings described herein are in conjunction with various embodiments for illustrative purposes, it is not intended that these teachings be limited to such embodiments. On the contrary, the teachings described and illustrated herein encompass various alternatives, modifications, and equivalents, without departing from the embodiments, the general scope of which is defined in the appended claims.

Except to the extent necessary or inherent in the processes themselves, no particular order to steps or stages of methods or processes described in this disclosure is intended or implied. In many cases the order of process steps may be varied without changing the purpose, effect, or import of the methods described.

A) Method for Multimodal Tissue Imaging Based on Resonance Raman Effect on Metal Based MRI Contrast Agents The present method and system uses a contrast imaging agent that can provide imaging contrast for both MRI and optical imaging. By independently measuring spatial distribution of such a contrast agent within a tissue using MRI and optical images, spatial correlations between the MRI and optical images can be established. Moreover, since some of the existing MRI contrast agents have tendency to accumulate in tumor tissues, intra-operative optical detection of such contrast agents can facilitate identification and resection of such tissues.

When introduced into the body prior to an imaging exam, MRI contrast materials make certain structures or tissues in the body appear different on the images than they would if no contrast material had been administered; so, contrast materials help distinguish or "contrast" selected areas of the body from surrounding tissue. By improving the visibility of specific organs, blood vessels or tissues, contrast materials help physicians diagnose medical conditions.

The mechanism of action of MRI contrast agents is that they typically change the value of T1 of nearby water protons thereby altering the contrast in the image. As such, this mechanism is general and the contrast can be detected by any standard MRI device.

There are different types of MRI contrast agents. Currently, the most common types used in neurosurgeries are chelates of metal ions (predominantly paramagnetic metal gadolinium Gd3+). In such chemical compounds, the metal ion is bonded to a ligand (typically organic) at two or more points. This is done typically to isolate the toxic metal ion and prevent its direct interaction with tissues. The present system and method uses these types of contrast agents. These contrast agents accumulate in tumor tissues by perfusion that result from the neovascularization of tumors and their penetration through the blood-brain barrier. This increased concentration provides contrast enhancement of tumor sections on MRI images.

Besides MRI, other techniques are used for tissue imaging. Optical imaging techniques are especially useful for intra-operative applications since these techniques are fast and non-invasive. Raman spectrometry is a particular optical imaging technique where a monochromatic excitation light in-elastically scatters of the vibrational transitions in the tissue. The scattered light has energies of these vibrational transitions imprinted in its spectrum which makes tissue identification possible. Standard Raman spectrometry is very informative but it has a practical problem in that Raman signals are typically very weak which requires long acquisitions and complex data analysis.

In recent years, there have been efforts to develop multimodal imaging contrast agents. These multimodal contrast agents provide simultaneous contrast for different imaging modalities (MRI, ultrasound, Raman spectroscopy, etc.). This is advantageous since simultaneous contrast makes correlations between different imaging modalities possible thus increasing the overall informational content. One such multimodal contrast agents is disclosed in: Kircher, Moritz F., et al. "A brain tumor molecular imaging strategy using a new triple-modality MRI-photoacoustic-Raman nanoparticle." Nature medicine 18.5 (2012): 829-834. All multimodal contrast agents that combine MRI and optical modalities that have been disclosed so far are based on nanoparticles. While such approach shows great promise, this technology is still in the research phase and translation to clinical use can be long and uncertain.

Multimodal imaging method based on optical detection of existing chelated ion MRI contrast agents has not been done so far.

Figure 2:
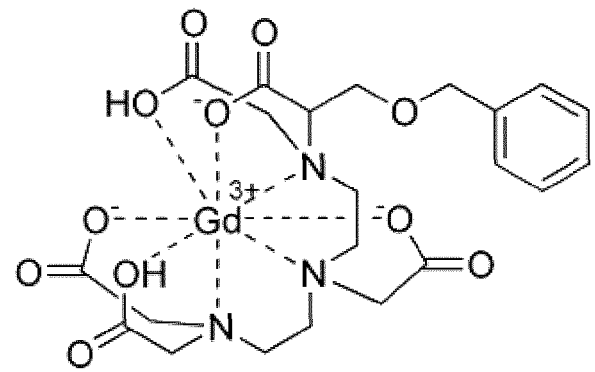
FIG. 2 shows the chemical structure of the gadolinium based contrast agent gadobenic acid.
Figure 3:
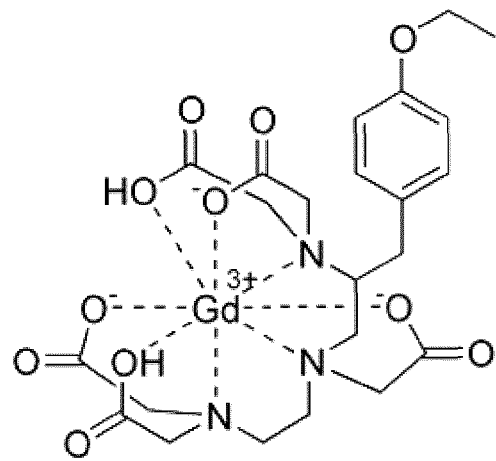
FIG. 3 shows the chemical structure of the gadolinium based contrast agent gadoxetic acid.
Figure 4:
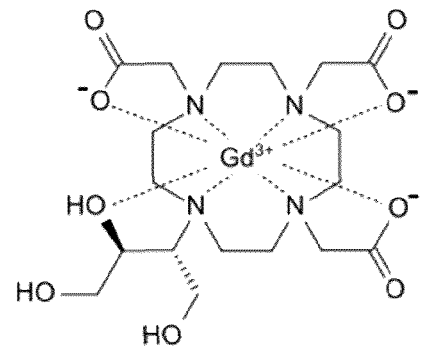
FIG. 4 shows the chemical structure of the gadolinium based contrast agent gadobutrol.

The present method is based on the use of metal based contrast agents typically used for MRI. Such contrast agents contain metal atoms, metal ions, or metal complexes where these metal entities are surrounded by ligands. Gadolinium based MRI contrast agents belong to this class. Examples of gadolinium based contrast agents are guadoteridol whose structure is schematically shown on FIG. 1; gadobenic acid whose structure is schematically shown on FIG. 2; gadoxetic acid whose structure is schematically shown on FIG. 3; and gadobutrol whose structure is schematically shown on FIG. 4. Other examples of metal based MRI contrast agents are those based on iron oxide, iron platinum, or manganese mention a few, which will be known to those skilled in the art.

In such structures, the charge-transfer (CT) transitions of the metal entity enhance THE metal-ligand stretching modes, and usually some of modes associated with the ligands alone. If an excitation optical source is tuned close to one of the charge-transfer electronic transitions, the vibrational modes associated with that particular transition exhibit increased Raman scattering coefficients due to resonance effects resulting in strong Raman scattering signals. By measuring these Raman signals it is possible to determine spatial the distribution of such metal based contrast agent close to the tissue surface and then this spatial distribution can be correlated with MRI images of the same contrast agent acquired independently.

The present method of multimodal imaging of tissue during a medical procedure after the tissue has been exposed involves the following steps.

1. Upon exposure of the tissue being operated on, a contrast agent is administered to the tissue within a water solution that may contain other chemicals that facilitate the contrast agent absorption or reduce its side effects. An example for such solution is ProHance. Each mL of ProHance contains 279.3 mg gadoteridol, 0.23 mg calteridol calcium, 1.21 mg tromethamine and water. The appropriate concentrations of the contrast agent and the amounts of the corresponding water solution delivered to the tissue are defined and provided by the contrast agent manufacturer or FDA. The contrast agent solution is administrated most often by injecting it into a blood vessel (vein or artery) but it is also possible to provide it orally or to inject it rectally. The typical distribution and elimination half-lives (reported as mean±SD) are 10-20 min and 1.5-2 hours, respectively. If the contrast agent is re-administered during the surgery, the total dose should be below the limit prescribed by the contrast agent manufacturer and FDA.
2. The relevant portion of the patient's body is then imaged by MRI whereupon the contrast agent provides imaging contrast enhancement over the same tissue being imaged but without the contrast agent present. The MRI imaging data is saved in computer memory. During the surgery, the 3D profile of the MRI image recorded in computer memory is registered to the physical patient body by using fiduciary markers, anatomical landmarks, or 3D scans. These registration techniques are known to a person skilled in the art and they allow 1:1 dynamic mapping of the physical space (patient body and surgical tools) onto a rendered computer image that includes MRI data. In this way, the surgeon is capable to orient herself/himself relative to internal patient's tissues and to identify the tissues that he sees more easily. The acquired MRI imaging data is stored in a memory storage device and in contains coordinates of the contrast agent distribution. Exemplary non-limiting methods of registration techniques are disclosed in U.S. National Phase patent application Ser. No. 14/655,814, entitled: "SYSTEMS AND METHODS FOR NAVIGATION AND SIMULATION OF MINIMALLY INVASIVE THERAPY"; Filing Date: 26 Jun. 2015, which is incorporated herein by reference in its entirety, and which are discussed herein after.
3. The exposed tissue is then illuminated with excitation light that has spectral components that are approximately tuned close to at least one of the charge-transfer electronic transitions of the contrast agent. The interaction of the excitation light with the charge-transfer electronic transitions produce Raman optical signals corresponding to vibrational transitions coupled to the charge-transfer electronic transitions that are enhanced due to Raman resonance effects. These Raman optical signals are detected and analyzed by a Raman spectral analyzer. The resonant Raman transition of the contrast agent can be identified beforehand in an experiment where Raman spectra of the pure contrast agent solution is measured using standard spectroscopic techniques.

During the surgery, there could be additional administration of the contrast agent and additional MRI performed scans while the patient's internal tissues are exposed so the sequence of the steps 2 and 3 can be reversed. Thus it will be appreciated that the order of steps 2 and 3 may be reversed, so that it does not matter whether the MRI imaging data is acquired before or after acquisition of the Raman optical signal data. By independently measuring the spatial distribution of such contrast agents within a tissue using MRI and optical images, spatial correlations between MRI and optical images can be established. This can be accomplished in various embodiments described below.

Figure 5:
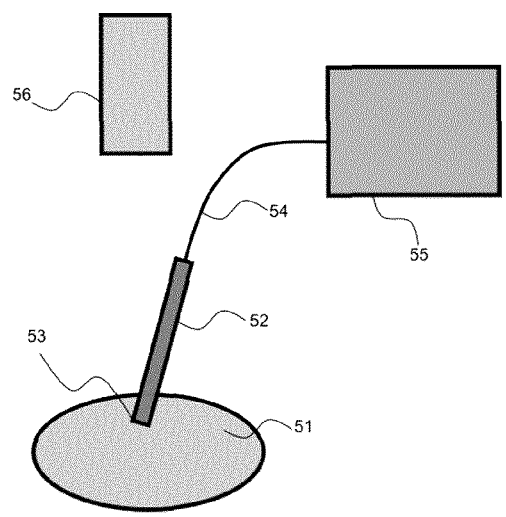
FIG. 5 shows an embodiment of a white light illumination system to allow a clinician to clearly observe the exposed tissue along with a Raman probe coupled to a Raman spectral analyzer through an optical fiber bundle and subsequently the Raman spectral analyzer analyzes the acquired Raman signals which are then registered or correlated with the MRI imaging data.

4. FIG. 5 shows a relevant portion of patient's tissue 51 that possibly contains a MRI contrast agent with chelated metal ions. The exposed tissue 51 is monitored by the surgeon through a white light imaging system 56. The imaging system can be a surgical microscope or imaging optics equipped with a digital camera that transfers the optical image to a display and/or saves the acquired images in computer memory. The white light images acquired through the optical imaging system 56 are registered with acquired MRI images or imaging data using fiduciary marks, anatomical landmarks, or 3D scans. Such registering techniques are known to a person skilled in the art. A handheld Raman probe that operates in the contact mode is used to interrogate tissue 51 is coupled to a Raman spectral analyzer 55 through an optical fiber bundle 54 and subsequently the Raman spectral analyzer 55 analyzes the acquired Raman signals.

An example of a Raman detection system containing a handheld Raman probe and a Raman analyzer can be found in Shim, Martin G., et al. "In vivo Near-infrared Raman Spectroscopy: Demonstration of Feasibility During Clinical Gastrointestinal Endoscopy" Photochemistry and photobiology 72.1 (2000): 146-150.

The intensity of Raman spectral components in the acquired Raman signal that corresponds said charge-transfer electronic transitions is proportional to the local contrast agent concentration. The surgeon can observe the position of the distal end 53 of the Raman probe 52 though optical imaging system 56 when Raman signal acquisition occurs and so can correlate the acquisition point with the white light images and subsequently register with MRI image through the registration process described above. In this way the spatial distribution of the contrast agent can be spatially correlated to the acquired MRI image.

Figure 6:
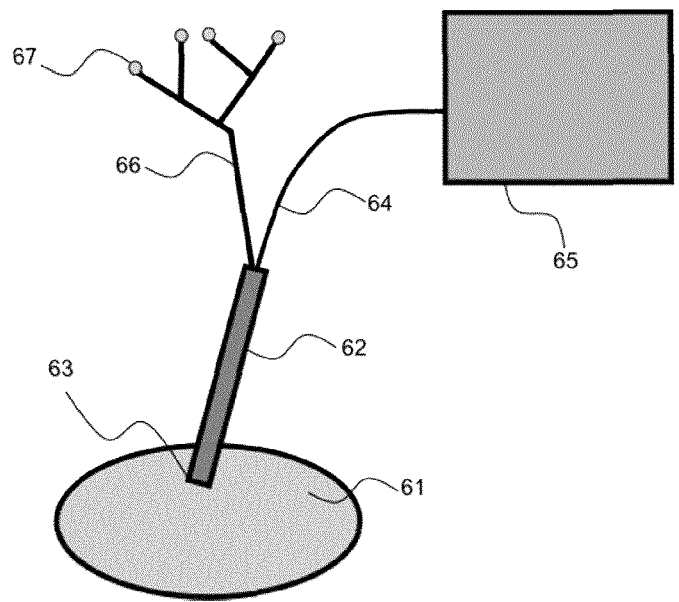
FIG. 6 shows an embodiment of the present system including a handheld Raman probe, a Raman spectral analyzer and a tracking tree that for facilitating tracking of the Raman probe.

FIG. 6 shows another possible embodiment. In this figure, the tissue section 61, handheld Raman probe 62, its probe distal end 63, optical fiber bundle 64, and Raman spectral analyzer 65 correspond to elements 51, 52, 53, 54, and 55 from FIG. 5, respectively. In addition, there is a tracking tree 66 that incorporates several solid balls 67 that are attached to tracking tree 66 in a rigid configuration. By detecting the position of solid balls using an infrared camera tracking system, the position of the distal tip 63 can be determined and spatially correlated to the MRI image (using tracking trees to spatially correlate with MRI is prior art and we will provide a few more details).

Figure 7:
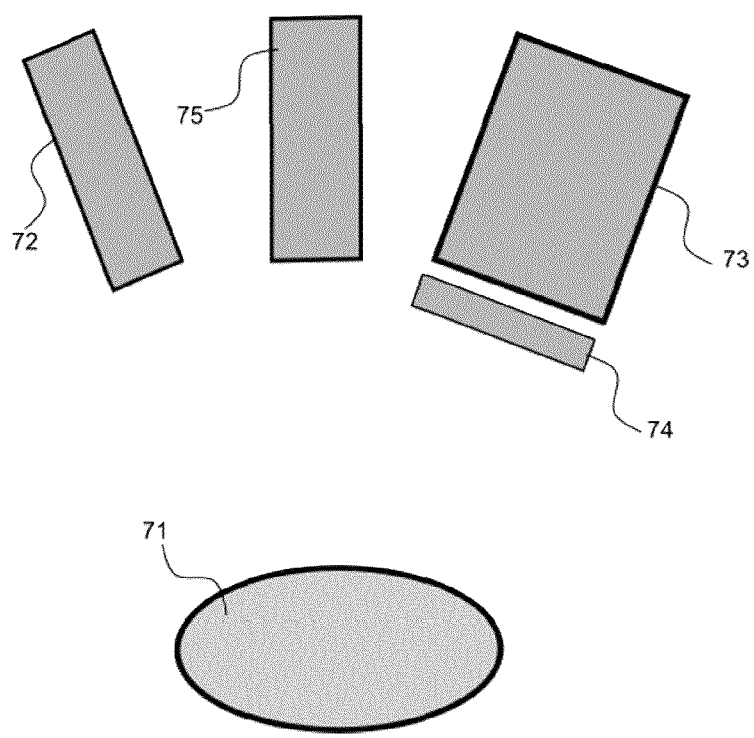
FIG. 7 shows another embodiment of an optical illumination and detection system coupled with a Raman detection system.

FIG. 7 shows another possible embodiment. The relevant portion of patient tissue 71 is observed under white light imaging system 75 that corresponds to optical imaging system 56 from FIG. 5. As described for the embodiment shown in FIG. 5, the white light images are registered to MRI images. A source of excitation light 72 that is tuned to at least one of the charge-transfer electronic transitions of the contrast agent is positioned in a way that portion of interest on tissue 71 is illuminated by the excitation light. The scattered light contains Raman spectral signals corresponding to the charged-transfer electronic transitions where these Raman signals are enhanced through resonance effects. This Raman signal is captured by a digital camera 73. An optical filter 74 is positioned in front of camera 73 so only relevant resonant Raman signal can pass through the filter in a significant amount and reach the detector of camera 73. The positions of cameras 72 and 73 are fixed in a rigid configuration relative to each other so it is possible to spatially register images of Raman signal distribution to the white light images and hence to the acquired MRI image using techniques described above.

A detailed description of an exemplary surgical system and registration of two or more imaging data sets is disclosed in U.S. National Phase patent application Ser. No. 14/655,814, entitled: "SYSTEMS AND METHODS FOR NAVIGATION AND SIMULATION OF MINIMALLY INVASIVE THERAPY"; Filing Date: 26 Jun. 2015, which is incorporated herein by reference in its entirety.

Figure 8:
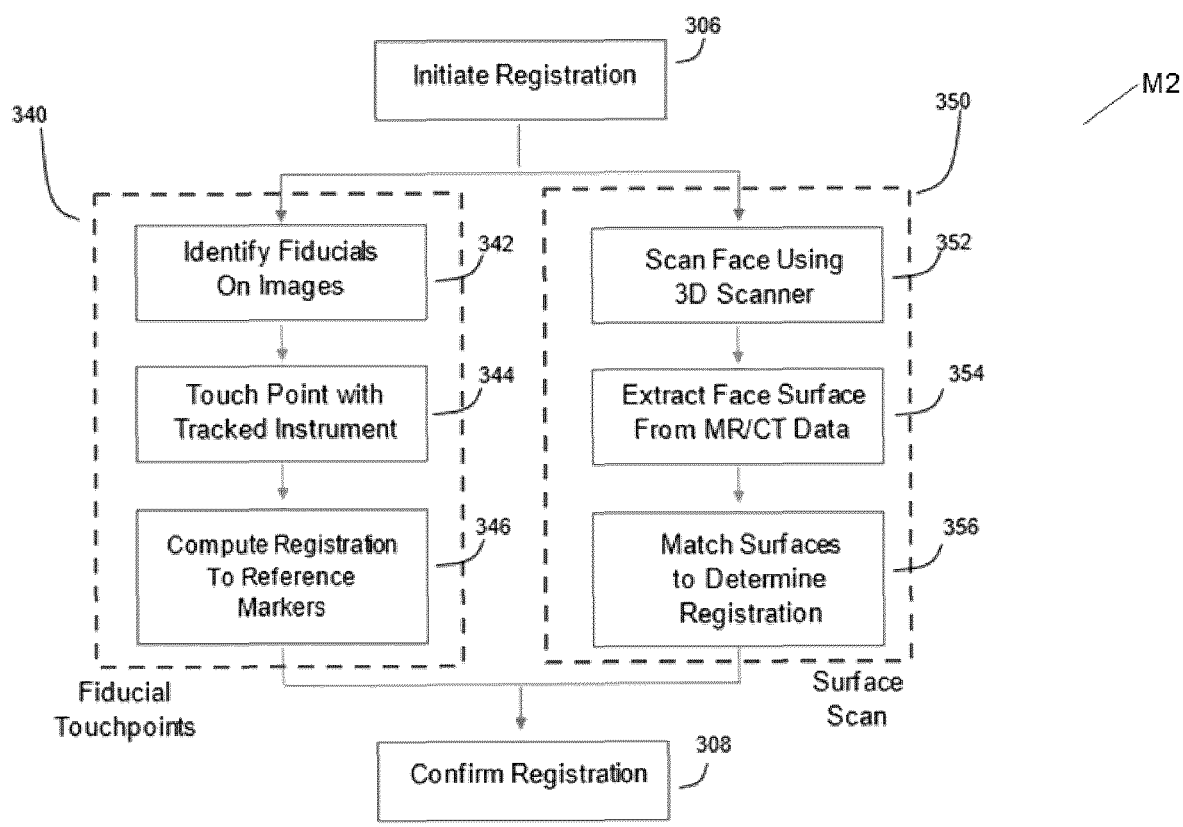
FIG. 8 is a flow diagram illustrating the steps followed for registering the multimodal imaging data from both MRI imaging and enhanced Raman imaging.

Exemplary medical procedures and registration of the MRI imaging data with the Raman imaging data is described hereinafter with respect to FIG. 8. Referring to FIG. 8, this block diagram illustrates a method of registration involving completing registration by using fiducial touch-points captured by a pointing tool as indicated by block 340, wherein completing registration by using fiducial touch-points comprises first identifying fiducial touch-points on images, as indicated by block 342, touching the fiducial touch-points with a tracked instrument, as indicated by block 344, and determining registration data in relation to reference markers, as indicated by block 346. The method alternatively further comprises: completing registration by conducting a surface scan procedure, as indicated by block 350, wherein conducting a surface scan procedure comprises scanning the face using a 3D scanner, as indicated by block 352, extracting the face surface data from MR/CT data, as indicated by block 354, and determining registration data points by matching the face surface data from the 3D scanner with the face surface data from MR/CT data, as indicated by block 356. Upon completing registration by using fiducial touch-points procedure, as indicated by block 340, or surface scan completing registration by conducting a surface scan procedure, as indicated by block 350, and transforming and confirming the determined registration data, as indicated by block 308.

During a navigation procedure, a handheld instrument is trackable by using a tracking system, and a representation of the instrument's position and orientation may be provided and displayed as an overlay on a previously acquired or current image (such as a three-dimensional scan) of a patient's anatomy obtained with an imaging device or system (such as ultrasound, CT or MRI). To achieve this, a registration is needed between the coordinate frame of a tracking system, the physical location of the patient in space, and the coordinate frame of the corresponding image of the patient.

This registration is typically obtained relative to a tracked reference marker, which is placed in a fixed position relative to the patient anatomy of interest and thus can be used as a fixed reference for the anatomy. Generally, this can be accomplished by attaching the reference to a patient immobilization frame (such as a clamp for skull fixation in neurosurgery), which itself is rigidly attached to the patient. However, the reference may be held to the frame, for example, through an arm, which can be bumped and accidentally moved, which creates a loss of registration. The reference marker is positioned so that it is visible by the navigation hardware (typically requiring line-of-sight for optical tracking, or otherwise within the observation or communication field of the tracking system, and this tends to position the reference such that it is in the open thus more susceptible to accidental interaction and loss of registration. In situations of lost registration, a surgical procedure tends to be stopped while a new registration is computed, although this may not always be possible if, for example, the registration fiducial-points or patient skin surface are no longer accessible due to the progression of the surgical procedure, and thus creating a need for a full re-registration or, in some cases even disabling navigation for the remainder of the procedure.

In an embodiment the method of registering the MRI and Raman imaging data is performed as follows:

prior to a surgical procedure, obtaining a preoperative image of patient tissue at a computing device using a MRI imaging device;

storing the preoperative image in a memory of the computing device;

during the surgical procedure, registering a Raman imaging device with a surgical navigation system [using optical tracking markers];

during the surgical procedure, obtaining an intraoperative image of the contrast agent distribution of the patient tissue at the computing device using the Raman imaging device;

correlating/registering the pre-operative image of the patient tissue with the intraoperative image of the patient tissue based on similar features provided by the navigation system data; and storing the transformation in the memory in association with one of the intraoperative image and the preoperative image.

Figure 9:
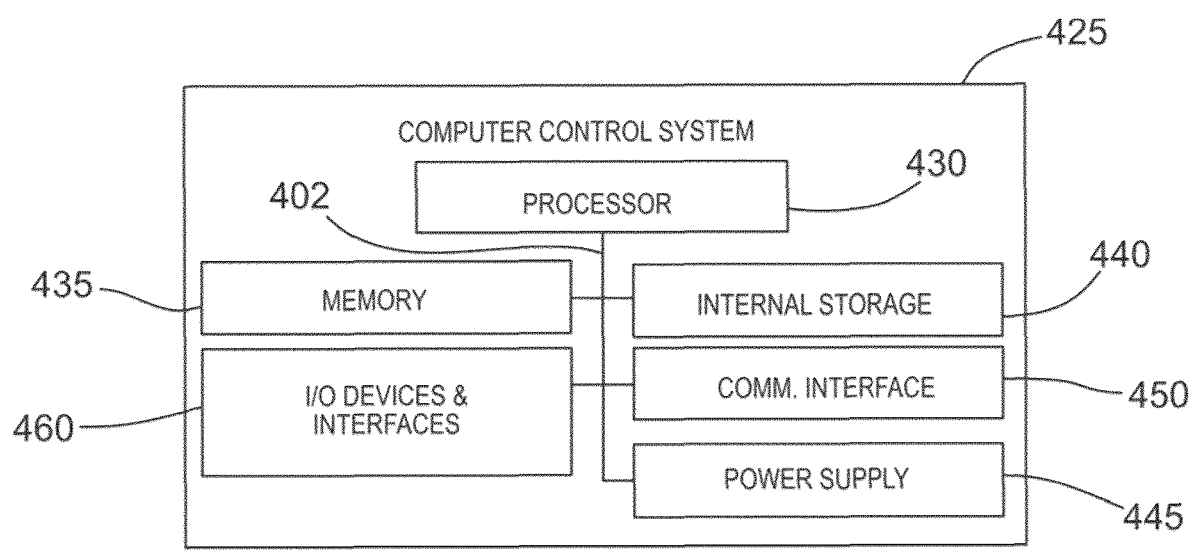
FIG. 9 shows an exemplary, non-limiting implementation of computer control system for implementing the multimodal tissue imaging method and system based on MRI and the resonance Raman effect.

FIG. 9 provides an exemplary, non-limiting implementation of computer control system 425, which includes one or more processors 430 (for example, a CPU/microprocessor), bus 402, memory 435, which may include random access memory (RAM) and/or read only memory (ROM), one or more internal storage devices 440 (e.g. a hard disk drive, compact disk drive or internal flash memory), a power supply 445, one more communications interfaces 450, and various input/output devices and/or interfaces 460 such as a user interface for a clinician to provide various inputs, run simulations etc.

Although only one of each component is illustrated in FIG. 8, any number of each component can be included computer control system 425. For example, a computer typically contains a number of different data storage media. Furthermore, although bus 402 is depicted as a single connection between all of the components, it will be appreciated that the bus 402 may represent one or more circuits, devices or communication channels which link two or more of the components. For example, in personal computers, bus 402 often includes or is a motherboard.

In one embodiment, computer control system 425 may be, or include, a general purpose computer or any other hardware equivalents configured for operation in space. Computer control system 425 may also be implemented as one or more physical devices that are coupled to processor 430 through one of more communications channels or interfaces. For example, computer control system 425 can be implemented using application specific integrated circuits (ASIC). Alternatively, computer control system 425 can be implemented as a combination of hardware and software, where the software is loaded into the processor from the memory or over a network connection.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Figure 10A:
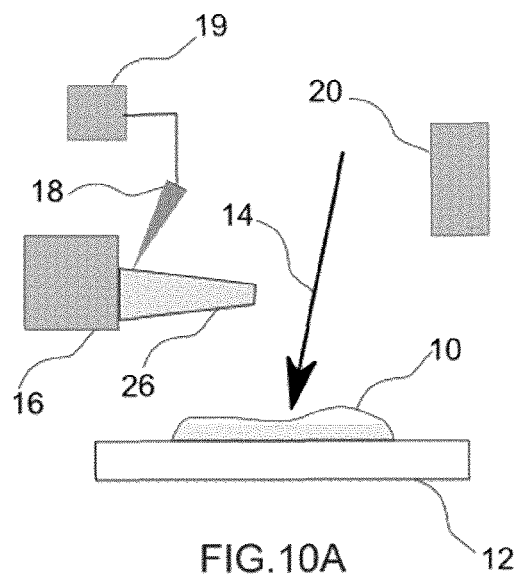
FIGS. 10A to 10D show schematic representations a combined laser ablation/mass spectrometer apparatus in which a liquid sample on a substrate is being irradiated by a laser (10A) to produce a superheated portion of the liquid sample (10B) which undergoes ablation (10C) to form a laser plume and a gas jet in the vicinity of the sample contains dopant molecules which are ionized by a sharp metal electrode which forms a corona discharge in which the ionized dopant molecules transfer their charges to some of the sample molecules within laser plume (10D).
Figure 10B:
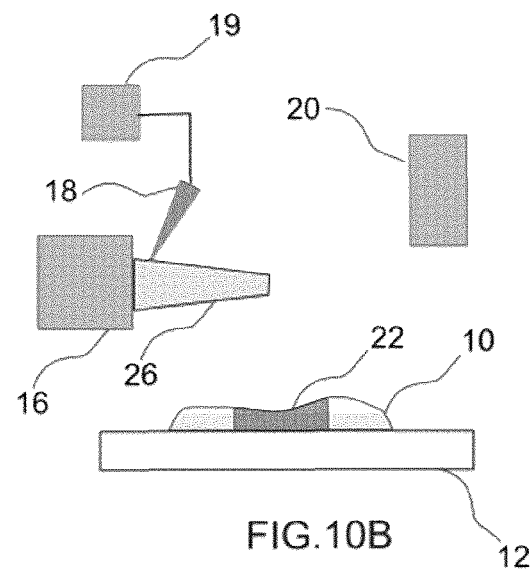
Figure 10C:
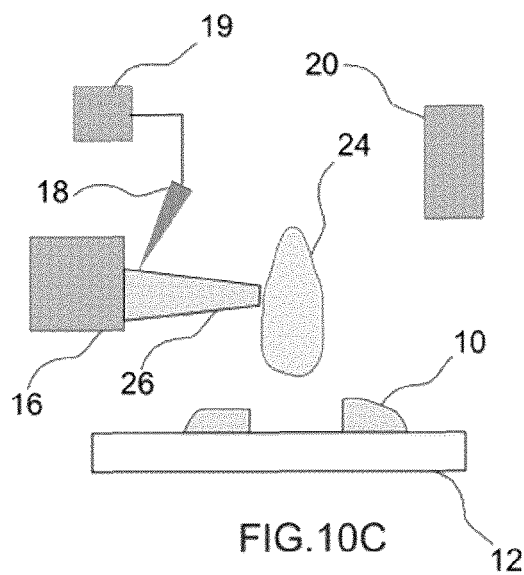
Figure 10D:
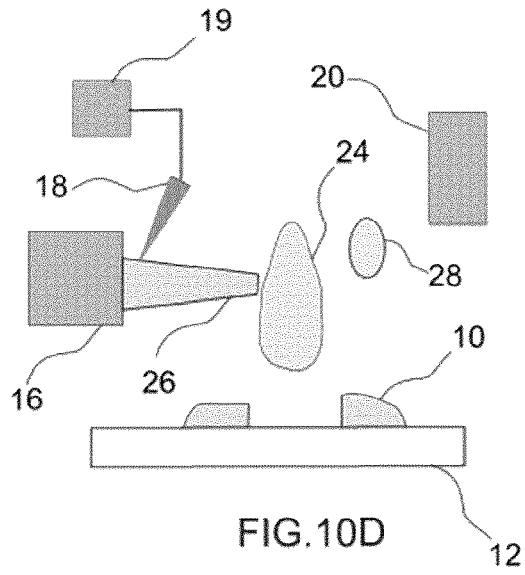

B) Method for Ionizing Laser Plumes Through Atmospheric Pressure Chemical Ionization Referring to FIGS. 10A to 10D, a sample 10 in the condensed phase is deposited on a sample holder 12. A laser pulse 14 is directed at sample 10 where the laser pulse 14 is absorbed thus creating a superheated portion 22 of the sample 10 as shown in FIG. 10B. The superheated portion 22 gets ablated creating a laser plume 24 (see FIG. 10C) that is generally an aerosol consisting of gas phase sample molecules, gas phase matrix molecules, molecular aggregates, small sample droplets, etc. A source 16 that creates a gas jet 26 is placed in the vicinity of the sample where the gas jet 26 contains dopant molecules. Close to the outlet of the gas jet 26 there is a sharp metal object 18 that is in electrical contact with a high voltage source 19. Due to the high voltage at the sharp tip of the sharp metal object 18, a corona discharge is formed ionizing some of the dopant molecules within the laser jet 26. Such ionized dopant molecules travel with jet 26 which is directed in a way to intercept laser plume 24. Some of these ionized dopant molecules transfer their charges to some of the sample molecules of interest within laser plume 24. Such ionized sample molecules form a cloud 28 which is directed towards a mass spectrometer 20 where these sample molecules are analyzed.

Figure 11A:
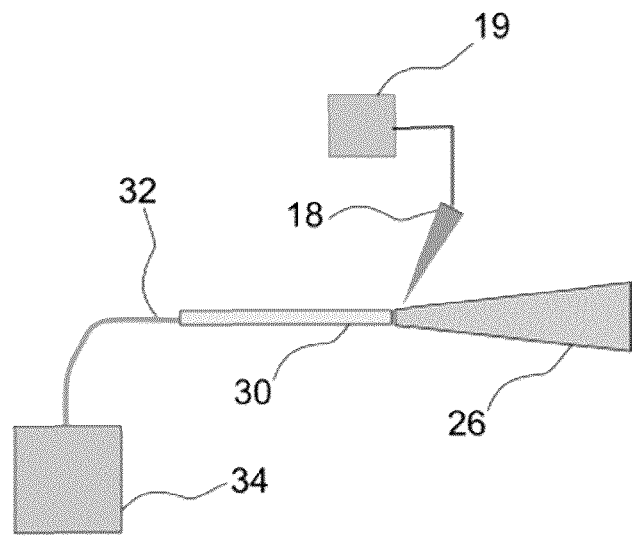
FIG. 11A shows a schematic drawing of an exemplary gas jet source forming part of the apparatus of FIGS. 10A to 10D.

Referring to FIG. 11A, the schematic shows an example of gas jet source 16. A pressured gas source (for example a gas cylinder or a compressor) 34 delivers a gas to a thin capillary 30 through a tubing 32. The gas passes through the capillary and exits at one of its ends creating a gas jet 26 corresponding to gas jet 26 from FIGS. 10A to 10D. Gas jet 26 is partially or completely ionized by a corona discharge created by sharp metal object 18 that is at high voltage provided by high voltage generator 19. High voltage generator 19 can provide constant high voltage or it can be modulated or pulsed in which case the frequency and phase of such modulation or pulsing should be synchronized to the ablative laser pulse in order to provide the optimal number of ions to the laser plume.

Figure 11B:
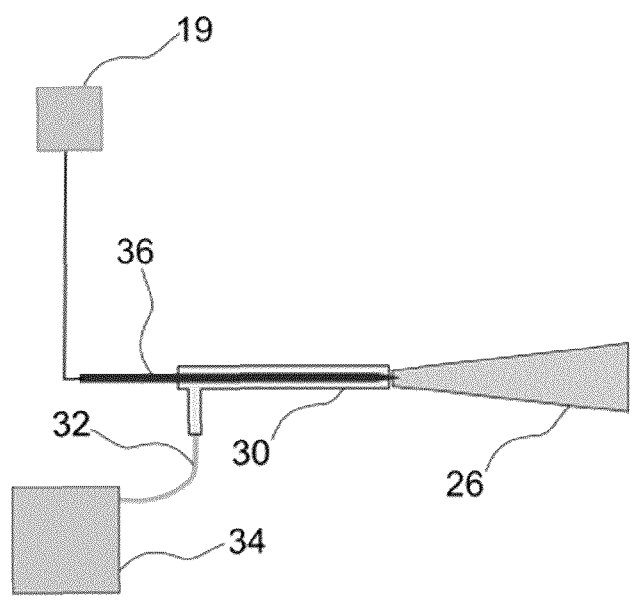
FIG. 11B shows a schematic drawing of another embodiment of a gas jet source forming part of the apparatus of FIGS. 10A to 10D.

FIG. 11B shows a possible variation of the system schematically presented in FIG. 11A. In this case, sharp metal object 18 from FIG. 11A has a form of a long needle 36 inserted inside capillary 30 where the sharp tip of needle 36 is positioned close to the capillary end where the gas exists forming gas jet 26. Needle 36 is at high voltage provided by high voltage generator 19 thus creates a corona discharge that partially or completely ionizes gas jet 26.

Figure 12A:
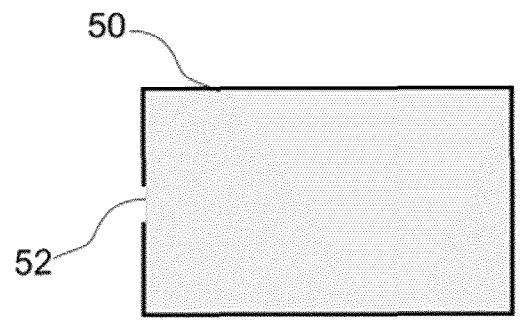
FIG. 12A shows a simple schematic of the mass spectrometer from FIG. 10A to 10D showing an orifice that is the entrance point for ions into mass spectrometer.

FIG. 12A shows a simple schematic of mass spectrometer 20 from FIGS. 10A to 10D, Mass spectrometer 20 has an orifice that is the entrance point for ions into mass spectrometer. Features and design principles of mass spectrometers and their orifices are known to the person having ordinary skill in the art.

Figure 12B:
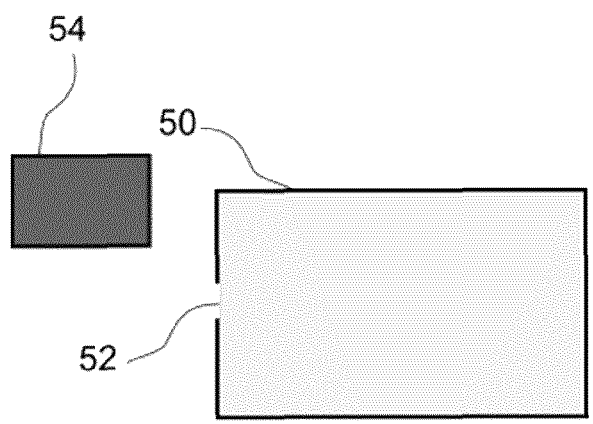
FIG. 12B shows an alternative embodiment of the system shown in FIG. 12A.

FIG. 12B shows a simple schematic of a system presented in FIG. 12A with an added feature 54 that corresponds to a system that provides static or/and dynamic electromagnetic fields that help guide the ion cloud 28 into mass spectrometer 50. Features and design principles of such electromagnetic systems are known to the person having ordinary skill in the art.

In summary, the present disclosure provides a mass spectrometry system for analyzing molecular composition of a sample in a condensed phase, comprising a pulsed laser capable of ablating the surface of said sample atmospheric pressure thereby producing an ablation plume containing analyte molecules; a gas delivery system for delivering a gas jet to the ablation plume, wherein the gas jet contains dopant molecules; a metal object with a sharp tip placed in the vicinity of said gas jet. The system includes a high voltage generator that is electrically connected to the metal object thereby creating a corona discharge at the sharp tip, wherein the corona discharge ionizes the dopant molecules in the gas jet. The gas jet is configured to intercept the laser ablation plume whereby at least one of subsequent direct or indirect collisions between the ionized dopant molecules and the analyte molecules results in ionization of several of the analyte molecules. The system includes directing the ionized analyte molecules towards a mass spectrometer wherein the ionized analyte molecules are analyzed providing information about a molecular composition of the sample.

The gas delivery system may include a capillary connected with a tubing connected to a source of compressed gas. The source of compressed gas may be a gas cylinder or gas compressor. The metal object with a sharp tip has a form of a sharp needle that is placed within the capillary. The dopant may be any one of air, water vapour, $N_2$, a noble gas, toluene, or a mixture of any of these gases. The high voltage source is any one of a pulsed, modulated, or constant high voltage source. The s gas delivery system jet may include a pulsed valve.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

What is claimed is:

1. A method for multimodal imaging during a medical procedure, the method comprising:
   administering a magnetic resonance imaging (MRI) contrast agent to tissue, the MRI contrast agent comprising at least one of a plurality of metal atoms, a plurality of metal ions, and a plurality of metal complexes, the MRI contrast agent comprising a chemical structure having a plurality of charge-transfer electronic transitions, the MRI contrast agent configured for use in relation to the multimodal imaging, and the multimodal imaging comprising MRI imaging, Raman imaging, and at least one selected from the group consisting of: computerized tomography (CT) imaging, ultrasound (US) imaging, white light imaging, and three-dimensional (3D) optical imaging;
   imaging the tissue with an MRI device, the MRI contrast agent facilitating enhancement of imaging contrast, thereby facilitating recordation of MRI imaging data;

tuning excitation light to approximate each charge-transfer electronic transition of the plurality of charge-transfer electronic transitions of the MRI contrast agent, thereby providing an excitation light with a plurality of spectral components tuned to each charge-transfer electronic transition of the plurality of charge-transfer electronic transitions;

illuminating the tissue with the tuned excitation light;

wherein interaction of the tuned excitation light with the plurality of charge-transfer electronic transitions produces a plurality of Raman optical signals by way of at least one Raman resonance effect;

detecting and analyzing the plurality of optical Raman signals to generate Raman imaging data; and registering the MRI imaging data with the Raman imaging data and with at least one of CT imaging data, US imaging data, white light imaging data, and 3D optical imaging data, wherein registering is a spatial registration using one of fiduciary markers or anatomical landmarks;

wherein administering the MRI contrast agent comprises administering a chelated metal ion material consisting of at least one of: a chelated gadolinium ion material, a chelated iron ion material, and a chelated manganese ion material, and a chelated platinum ion material, and and wherein administering the MRI contrast agent further comprises administering at least one of: a gadoteridol, a gadobenic acid, a gadoxetic acid, and a gadobutrol.

2. The method of claim 1, wherein illuminating is performed prior to imaging.

3. The method of claim 1, wherein registering comprises, by using a computing device having a memory:

prior to a surgical procedure, obtaining a preoperative image of the tissue from the MRI device;

storing the preoperative image in the memory;

during the surgical procedure, registering a Raman imaging device with a surgical navigation system;

during the surgical procedure, obtaining an intraoperative image of an MRI contrast agent distribution of the tissue by using the Raman imaging device;

at least one of correlating and registering the pre-operative image of the tissue with the intraoperative image of the tissue based on corresponding features provided by navigation data from the surgical navigation system; and storing a transformation in the memory in association with one of the intraoperative image and the preoperative image.

4. The method of claim 1, wherein detecting and analyzing comprises using a Raman spectral analyzer.

5. The method of claim 4, wherein using Raman spectral analyzer comprises using a spectrometer.

6. A computer-implemented method for multimodal imaging and registration during a medical procedure, using a computing device having a memory, the method comprising:

administering a magnetic resonance imaging (MRI) contrast agent to tissue, the MRI contrast agent comprising at least one of a plurality of metal atoms, a plurality of metal ions, and a plurality of metal complexes, the MRI contrast agent comprising a chemical structure having a plurality of charge-transfer electronic transitions, the MRI contrast agent configured for use in relation to the multimodal imaging, and the multimodal imaging comprising MRI imaging, Raman imaging, and at least one selected from the group consisting of: computerized tomography (CT) imaging, ultrasound (US) imaging, white light imaging, and three-dimensional (3D) optical imaging;

imaging the tissue with an MRI device, the MRI contrast agent facilitating enhancement of imaging contrast, thereby facilitating recordation of MRI imaging data;

tuning excitation light to approximate each charge-transfer electronic transition of the plurality of charge-transfer electronic transitions of the MRI contrast agent, thereby providing an excitation light with a plurality of spectral components tuned to each charge-transfer electronic transition of the plurality of charge-transfer electronic transitions;

illuminating the tissue with the tuned excitation light, wherein interaction of the tuned excitation light with the plurality of charge-transfer electronic transitions produces a plurality of Raman optical signals by way of at least one Raman resonance effect;

detecting and analyzing the plurality of optical Raman signals to generate Raman imaging data; and registering the MRI imaging data with the Raman imaging data and with at least one of CT imaging data, US imaging data, white light imaging data, and 3D optical imaging data, wherein administering the MRI contrast agent comprises administering a chelated metal ion material consisting of at least one of: a chelated gadolinium ion material, a chelated iron ion material, and a chelated manganese ion material, and a chelated platinum ion material, and and wherein administering the MRI contrast agent further comprises administering at least one of: a gadoteridol, a gadobenic acid, a gadoxetic acid, and a gadobutrol.

7. The method of claim 6, wherein registering comprises, by using the computing device, prior to a surgical procedure, obtaining a preoperative image of the tissue from the MRI device;

storing the preoperative image in the memory;

during the surgical procedure, registering a Raman imaging device with a surgical navigation system;

during the surgical procedure, obtaining an intraoperative image of an MRI contrast agent distribution of the tissue by using the Raman imaging device;

at least one of correlating and registering the pre-operative image of the tissue with the intraoperative image of the tissue based on corresponding features provided by navigation data from the surgical navigation system; and storing a transformation in the memory in association with one of the intraoperative image and the preoperative image.

* * * * *